United States Patent [19]

Bushatz et al.

[11] Patent Number: 5,226,891
[45] Date of Patent: Jul. 13, 1993

[54] SEAL PROTECTION APPARATUS

[75] Inventors: David C. Bushatz, Huntington Beach; Vincent C. Tangherlini, Rancho Santa Margarita, both of Calif.

[73] Assignee: Applied Medical Resources, Laguna Hills, Calif.

[21] Appl. No.: 864,571

[22] Filed: Apr. 7, 1992

[51] Int. Cl.⁵ ............................................. A61M 5/32
[52] U.S. Cl. .................................... 604/165; 604/274
[58] Field of Search ............ 604/164, 165, 158, 274, 604/157

[56] References Cited

U.S. PATENT DOCUMENTS

| | | | |
|---|---|---|---|
| 4,535,773 | 8/1985 | Yoon . | |
| 4,601,710 | 7/1986 | Moll | 604/165 |
| 4,654,030 | 3/1987 | Moll . | |
| 4,902,280 | 2/1990 | Lander . | |
| 4,931,042 | 6/1990 | Holmes | 604/164 |
| 5,030,206 | 7/1991 | Lander | 604/164 |
| 5,053,016 | 10/1991 | Lander . | |
| 5,066,288 | 11/1991 | Deniega . | |
| 5,129,885 | 7/1992 | Green et al. | 604/165 |
| 5,158,552 | 10/1992 | Borgia et al. | 604/165 |

Primary Examiner—Paul J. Hirsch
Attorney, Agent, or Firm—Richard L. Myers

[57] ABSTRACT

A trocar adapted to provide a working channel through a body wall and includes a cannula defining the channel along an axis between the distal and proximal ends of the cannula. A housing disposed at the proximal end of the cannula includes at least one elastomeric seal. An elongate obturator adapted to be moved in proximity to the seal includes a sharp distal tip and a sheath which protects the seal from the sharp tip during movement of the obturator through the working channel. This sheath is movable from a first position wherein it is releasably fixed to the obturator and a second position wherein it is releasably fixed to the housing to expose the shape tip distally of the cannula.

17 Claims, 4 Drawing Sheets

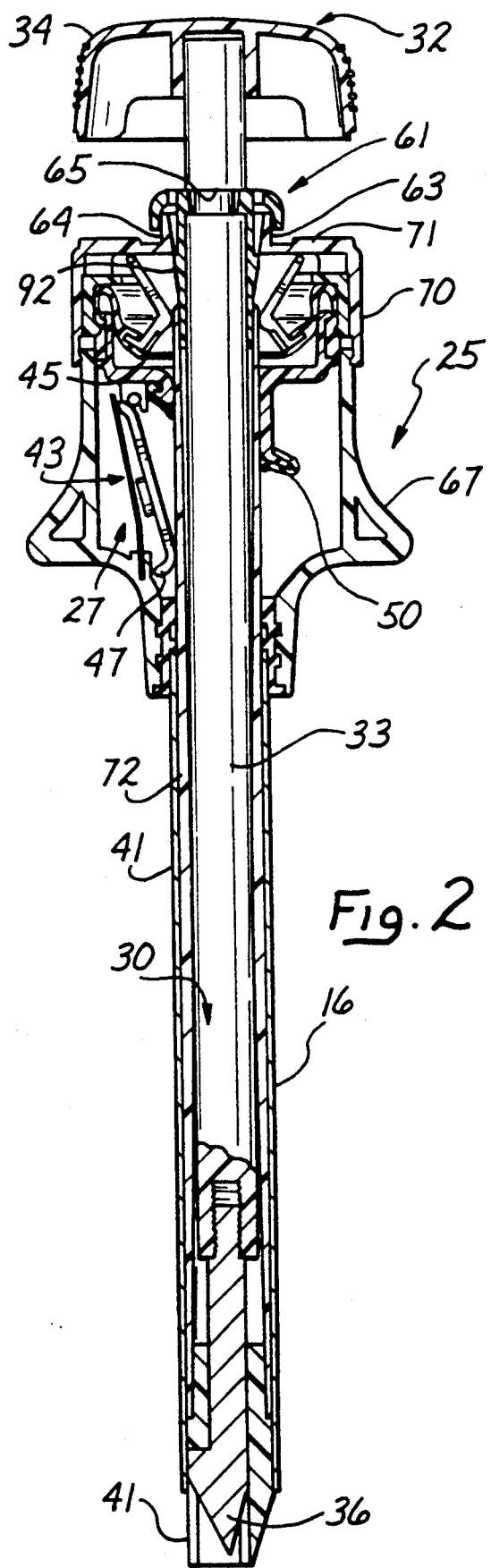
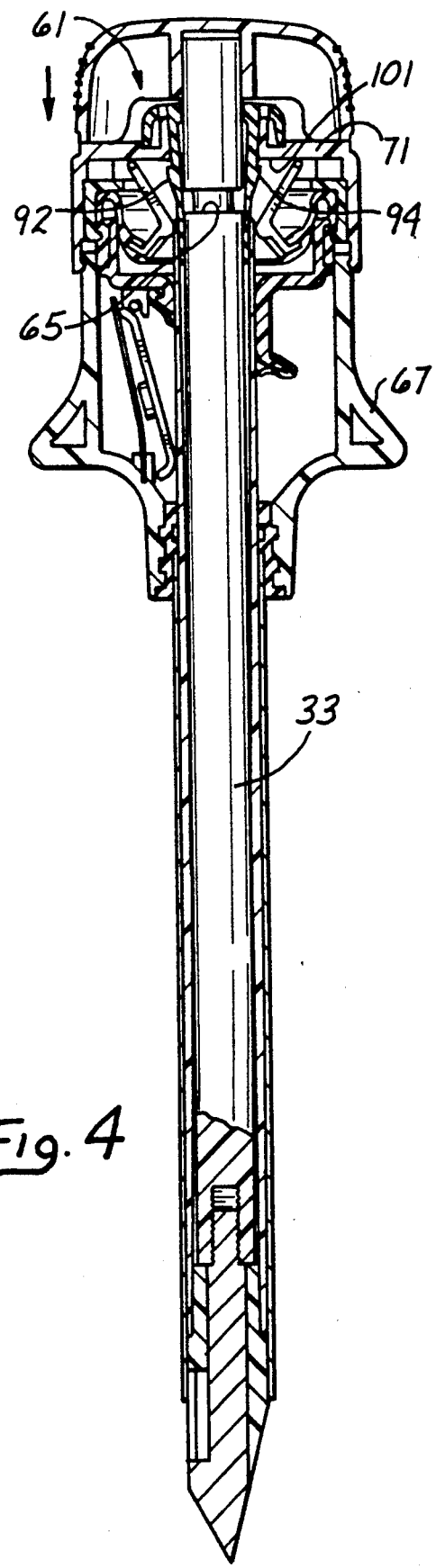
Fig. 2
Fig. 4

SEAL PROTECTION APPARATUS

BACKGROUND OF THE INVENTION

1. Field of the Invention

This invention relates generally to trocars and obturators and more specifically to devices for shielding the sharp tip of an obturator.

2. Discussion of the Prior Art

Mechanical trocars typically include a cannula defining a working channel and a housing for seals which inhibit the escape of insufflation gasses. The cannula of the trocar is adapted to be positioned across the abdominal wall of a patient using an obturator which is initially inserted into the working channel and then removed once the cannula is in place. This obturator is provided with a sharp distal tip which facilitates the puncture of the abdominal wall and permits the cannula to be moved into position through the resulting hole.

When the obturator is initially inserted into the cannula, it must pass through the seal mechanism at the proximal end of the working channel. If this sharp tip is not shielded, it can cut or otherwise damage the seals in the housing.

In the past, shields have been biased to a forward position covering the sharp tip during preliminary insertion of the obturator. As the tip and shield are moved against the abdominal wall, the sharp tip moves forward while the shield is forced rearwardly of the tip. As the hole is punched through the abdomen, the shield is free to follow its bias in the distal direction eventually covering the tip. This is a very complex mechanism and greatly increases the cost of manufacture. It also relies upon the abdominal wall and the surgeon to force the shield in the proximal direction in order to expose the tip. The magnitude of the required force is significant and must be continuously exerted on the shield during the puncture process.

SUMMARY OF THE INVENTION

In accordance with the present invention, a trocar is provided with an obturator shield which is considerably less expensive to manufacture, but it also provides for a simple structure which protects the seals during the preliminary introduction of the obturator into the working channel of the cannula. Furthermore, the present invention provides for the locking of the shield in a first position wherein the shield has a removably fixed relationship with the obturator, and a second position wherein the shield has a removably fixed relationship with the housing.

In accordance with one aspect of the invention, a trocar is adapted to provide a working channel through a body wall and comprises a cannula defining the working channel extending along an axis between a distal end and a proximal end of the cannula. A housing attached to the proximal end of the cannula encloses at least one seal. An elongated obturator adapted to move through the seal in the housing and through the working channel of the cannula is provided with a distal tip for puncturing the body wall. A sheath overlying the obturator is movable between a first position and a second position. In the first position, the sheath has a releasibly fixed relationship with the obturator and extends between the sharp tip and the seal to prevent damage to the seal by the sharp tip. In the second position, the shield has a fixed relationship with the housing and the obturator is movable relative to the sheath to expose the sharp tip distally of the cannula.

In another aspect of the invention a method for providing a wording channel across a body wall, includes the step of providing a subassembly including a trocar housing and a cannula forming the working channel, and a seal mechanism enclosed in the housing. The method further comprises the step of inserting into the working channel an obturator having an elongate shaft and a sharp distal tip. The seal mechanism is protected during the inserting step with a shield locked to the obturator in a first position wherein the shield is disposed between the sharp tip and the seal mechanism. The shield is unlocked from the obturator to expose the sharp tip and the body wall is punctured with a sharp tip to permit the cannula to cross the body wall. Finally, the obturator is removed from the cannula with the shield leaving the working channel in operative position across the body wall.

These and other features and advantages of the invention will be more apparent with a discussion of preferred embodiments and the best mode of the invention, taken in combination with the associated drawings.

DESCRIPTION OF THE DRAWINGS

FIG. 2 is an axial cross-section view of the trocar illustrated in FIG. 1 and showing the seal locked in a first position where it has a releasibly fixed relationship with the obturator;

FIG. 4 is an axial cross-section view similar to FIG. 2 illustrating the shield in a second position wherein the shield has a releasibly fixed relationship with the housing of the trocar;

FIG. 8 is an axial cross-section view of the locking mechanism associated with the obturator; and FIG. 9 is an end view of the locking mechanism taken along lines 9—9 of FIG. 8.

DESCRIPTION OF PREFERRED EMBODIMENTS

Figure 1:
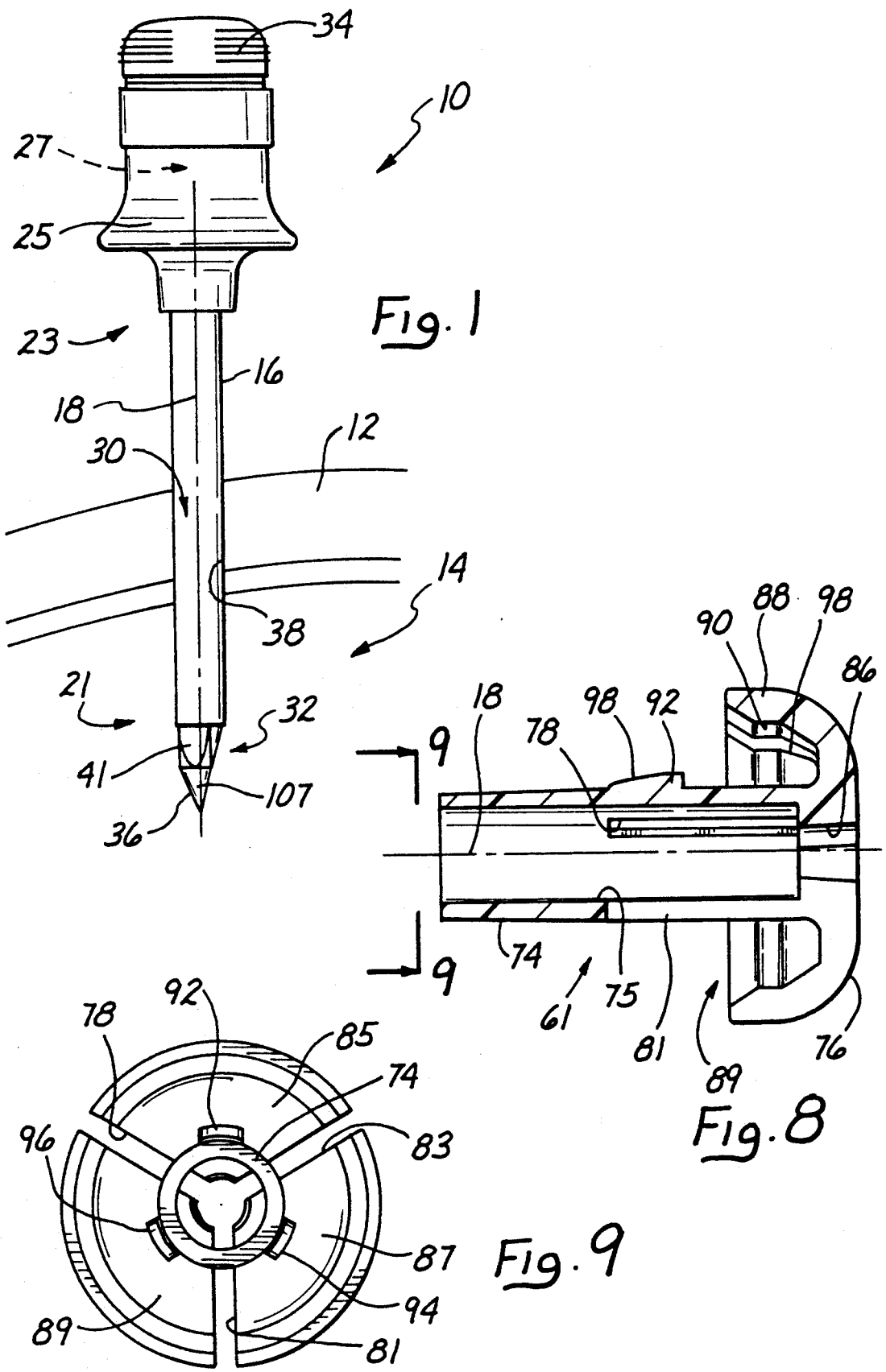
FIG. 1 is a side elevation view of the trocar with the cannula disposed in an operative position across the body wall.

A trocar is illustrated in FIG. 1 and designated generally by the reference numeral 10. The purpose of the trocar 10 is to establish a working channel across a body wall, such as the abdominal wall 12, from regions exterior of the body to regions interior of the body, such as the abdominal cavity 14. The trocar 10 is commonly used in laparoscopic surgery wherein the abdominal cavity 14 is pressurized with an insufflation gas in order to provide for organ separation and generally increase the amount of operative space. The trocar 10 includes a cannula 16 which extends along an axis 18 between a distal end 21 and a proximal end 23. At the proximal end 23, a housing 25 is attached to the cannula 16 and provides an enclosure for a seal mechanism 27 which will be described in greater detail with reference to FIG. 2.

When the trocar 10 is operatively disposed, these elements, the cannula 16, the housing 25 and seal mechanism 27, define a working channel 30 into the cavity 14. Various instruments are inserted through this channel 30 to perform operative functions in the cavity 14. It is the purpose of the seal mechanism 27 to block the escape of the insufflation gasses from the cavity 14 through the working channel 30 of the trocar 10, both when the instruments are inserted and when the instruments are removed.

Placing the cannula 16 in its operative position is accomplished by using an obturator 32 which has an elongate configuration, with a cap 34 disposed at its proximal end and a sharp tip 36 disposed at its distal end. It is the purpose of the obturator 32 to place the cannula 16 in its operative position across the abdominal wall 12. To accomplish this function, the obturator 32 is initially loaded into the working channel 30 by moving the sharp tip 36 through the seal mechanism 27 in the housing 25 and through the cannula 16. With the sharp tip 36 exposed distally of the cannula 16, the obturator 32 and cannula 16 are forced through the abdominal wall 12 to create a puncture or hole 38. When the hole 38 has been created and the cannula 16 is in its operative position, as illustrated in FIG. 1, the obturator 32 can be removed from the working channel 30 through the housing 25 and the seal mechanism 27, leaving these element in place.

Of particular interest to the present invention is a shield 41 which protects the seal mechanism 27 from being cut by the sharp tip 36 during placement or removal of the trocar 32 from the working channel 30.

Referring now to FIG. 2, the seal mechanism can take many different forms, but in the illustrated embodiment, a flapper valve 43 is provided along with a septum seal 45. This type of seal mechanism is disclosed in applicant's co-pending application Ser. No. 07/732,141 which is incorporated herein by reference. Generally, the septum seal 45 provides an annular seal around the obturator 32 or any instrument disposed in the working channel 30. Upon removal of the obturator 32, and in the absence of any instrument in the working channel, the flapper valve 43 provides a flapper 47 which forms a seal with a seat 50. Both the flapper valve 43 and the septum seal 45 provide means for preventing the escape of insufflation gases from the abdominal cavity 14.

These seals contain elastomeric materials and, in the case of the septum seal 45, are biased inwardly to engage any object moving through the working channel 30. In the absence of some barrier, such as the shield 41, the sharp tip 36 of the obturator 32 could damage the seals 43, 45. This damage could occur any time the sharp tip 36 is in proximity to the seals 43, 45, such as when the obturator 32 is inserted into or removed from the housing 25.

Figure 3:
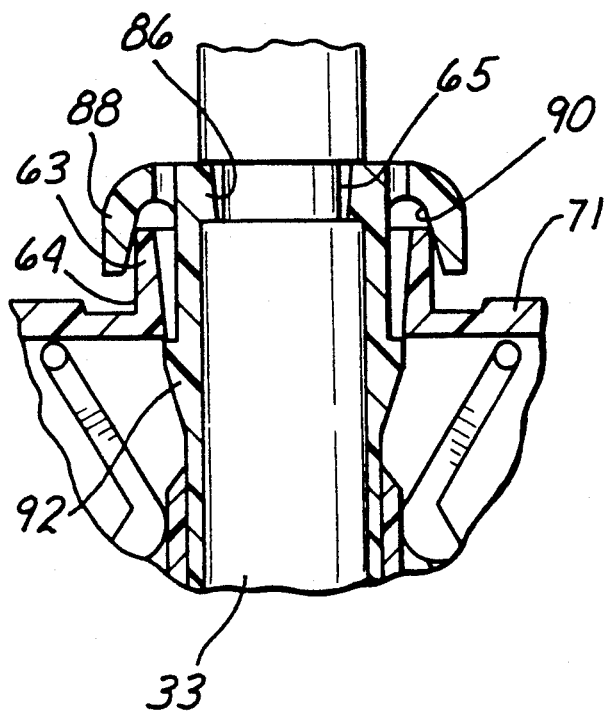
FIG. 3 is an enlarged view of a sheath locking mechanism as illustrated in FIG. 2.

Of particular interest to the present invention is the shield 41 which, in a first position best illustrated in FIGS. 2 and 3, is initially fixed to and carried by the obturator 32. With the shield 41 covering the sharp tip 36, the obturator 32 can be inserted into the working channel 30 of the housing 28 and cannula 16 without damaging the seals 43, 45. Once the sharp tip 36 is passed beyond the seals 43, 45, the shield 41 can be released from the obturator 32 thereby permitting the obturator 32 to be moved further distally to clear the shield 41 and exposed the sharp tip 36.

Figure 5:
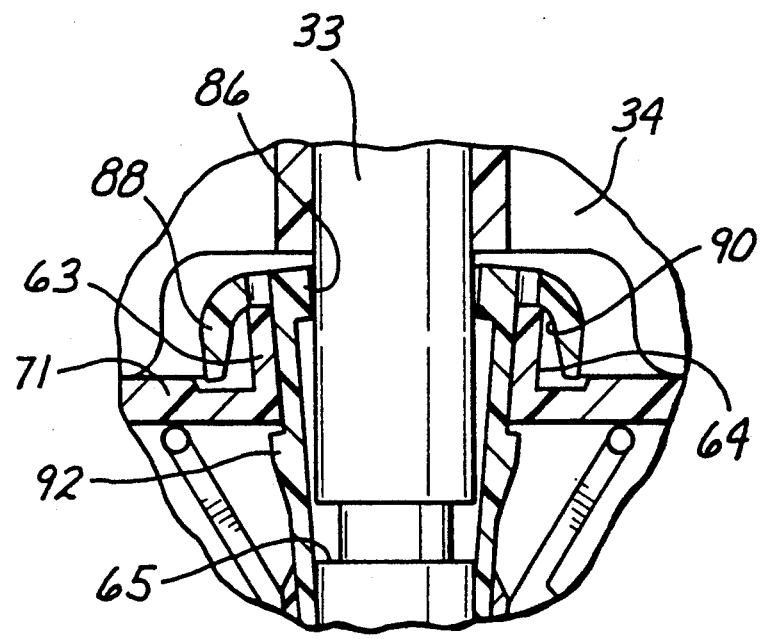
FIG. 5 is an enlarged view of the locking mechanism and housing illustrated in FIG. 4.

In this state, the shield is disposed in a second position where it has a fixed relationship with the housing 25, and the sharp tip 36 is exposed to facilitate puncture of the abdominal wall. This second position is best illustrated in FIGS. 4 and 5.

Movement of the shield 41 between its first and second positions is facilitated by the interrelationship of the obturator shaft 33, a locking device 61 associated with the shield 41, and an annular flange 63 associated with the housing 25. In accordance with the preferred embodiment, the shaft 33 of the obturator 32 is provided with an annular recess 65 which can be positioned generally anywhere along the length of the shaft. In the illustrated embodiment, the shield 41 is sufficiently long to extend from this recess 65 distally beyond the sharp tip 36.

The housing 25 in this embodiment includes a distal portion 67 and a proximal portion 70 which carries the seal mechanism 27. The annular flange 63 has an outer surface 64 and is disposed to extend generally axially proximally of an end wall 71 of the proximal portion 70.

The shield 41 includes an elongate tubular section 72 which extends distally of the locking device 61. The tubular section 72 has a wall thickness which is generally limited in its outside diameter by the inside diameter of the cannula 16 and limited in its inside diameter by the outside diameter of the shaft 33.

The locking device 61 is fixed to the tubular section 72 and has in a preferred embodiment the configuration illustrated in FIG. 8 and 9. In this embodiment, the locking device has an integral configuration consisting generally of an elongate tube 74, having an inner surface 75, which extends into a surrounding cap 76. The device 61 is divided along at least a portion of its length by slots which extend axially in the tube 74 and radially in the cap 76. These slots, designated by the reference numerals 78, 81, and 83 in FIG. 9, separate the locking device 61 into a plurality of sections 85, 87 and 89. The absence of material binding the sections 85, 87 and 89 together provides these sections with characteristics such that they can be moved a limited distance radially outwardly of the axis 18. However, these sections 85-89 are biased inwardly against this radial expansion.

Of particular interest to the present invention is a tongue 86 which extends radially inwardly of the surface 75 along each of the sections 85-89. This tongue 85 is preferably disposed in the distal regions of the locking device so that any radial movement of the sections 85-89 provides for the maximum degree of radial movement for the tongue 86. In the illustrated embodiment, the tongue 86 forms part of the cap 76 along with an annular flange 88 which extends generally axially distally along the tube 74. The flange 88 has an inner surface 90. Also associated with the locking device 61 are a plurality of lugs 92, 94 and 96 which extend outwardly of the tube 74 in each of the sections 85, 87, 89, respectively. An inclined surface faces distally outwardly of each of the lugs 92-96. For example in FIG. 8, the lug 92 is illustrated with an outer surface 98.

In operation, the shield 41, including the tubular section 72 and locking device 61, is fixed to the shaft 33 of the obturator 32 in the first position. This is accomplished by enabling the tongue 86 of the locking device 61 to engage the recess 65 as illustrated in FIG. 2. As further pressure is applied to move the cap 34 in the distal direction, the annular flange 88 of the locking device 61 engages the annular flange 63 associated with the housing 70. In a preferred embodiment, the flange 63 is disposed inwardly of the flange 88 and their respective surfaces 75 and 90 are brought into sliding engagement. One of these surfaces 75 and 90 is provided with an inclined configuration so that further distal movement of the locking device 61 relative to the housing 70, causes the outer flange 88 to ride up on the inner flange 63 thereby expanding the sections 85-89 radially outwardly. This outward expansion carries the tongue 86 outwardly until it eventually clears the recess 65 and rides up on the outer surface of the shaft 33. This second position of the locking device 61 enables the cap 34 to be moved further distally thereby exposing the sharp tip 36 beyond the tubular section 72 of the shield 41. In this configuration, best illustrated in FIG. 4, the trocar 10 is prepared for insertion through the abdominal wall 12.

In order to lock the shield 41 in the second position illustrated in FIG. 4, the housing is provide with an annular shoulder 101 which has a radius greater than the radius of the lugs 92-96 in the first position (illustrated in FIG. 3) but less than the radius of the lugs 92-96 in the second position (illustrated in FIG. 5). With these characteristics, the lugs 92-96 clear the shoulder 101 as the obturator 32 is being inserted. However, when the sections 85-89 of the locking device 61 expand radially outwardly to the second position, the flange 63 is held between the lugs 92-96 and the cap 76, effectively locking the shield 41 to the housing 25. The shield 41 cannot move further distally due to the interference between the flange 63 and the cap 34. Similarly, the shield 41 cannot move proximally due to the interference between the lugs 92-96 and the shoulder 101.

Figure 6:
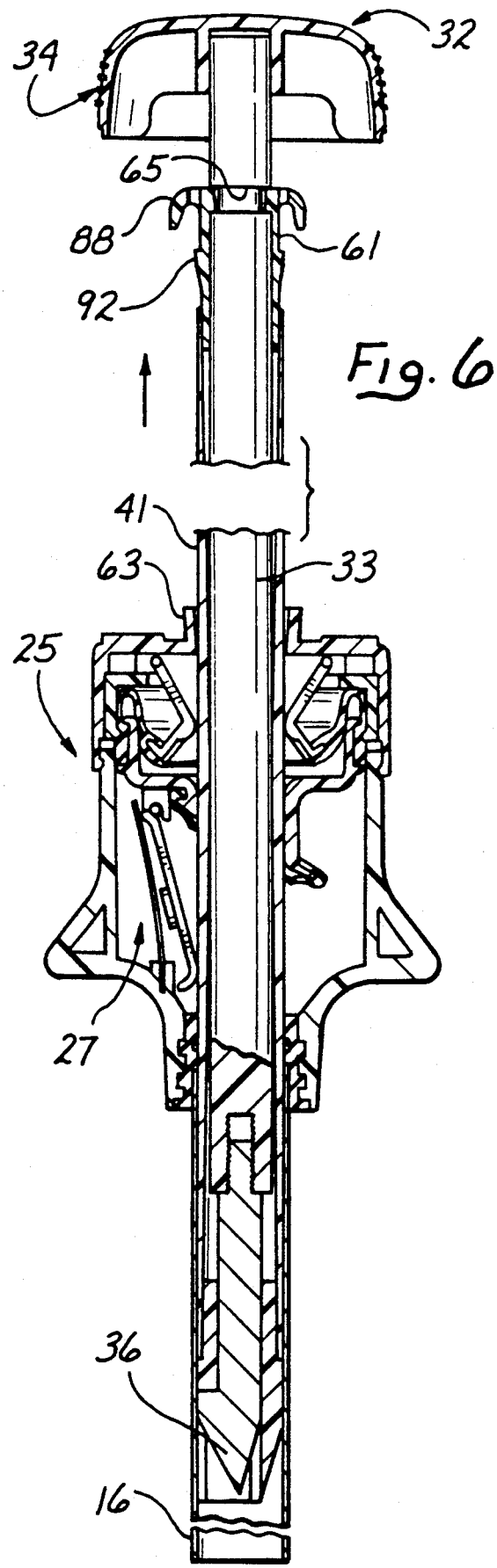
FIG. 6 is an axial cross-section view of the trocar with the obturator being removed from the housing.

With reference to FIG. 6, it will be apparent how this sequence of events is reversed as the obturator 32 is removed from the cannula 16. By engaging the cap 34 of the obturator 32 and the distal end 21 of the housing 25, the shaft 33 can be moved distally through the working channel 30. This will draw the annular recess 65 distally until it underlies the tongue 86. At this point, the tongue 86 will collapse into the recess 65 due to the natural bias of the sections 85-89 of the locking device 61. As the tongue 86 drops into the recess 65, the locking device moves to its first position wherein the lugs 92-96 clear the shoulder 101. Further proximal movement of the shaft 33 also moves the locking device 61 and associated shield 41 proximally, thereby permitting the outer flange 88 to disengage the inner flange 63. This facilitates the further collapse of the tongue 86 into the recess 65 again providing the firm locked relationship between the shield 41 and the shaft 33.

The initial proximal movement of the shaft 33 relative to the shield 41 moves the sharp tip 36 into the tubular section 72. In this position, the final removal of the obturator 32 from the housing 25 is accomplished with the seal mechanism isolated from the sharp tip 36 by the shield 41.

Figure 7:
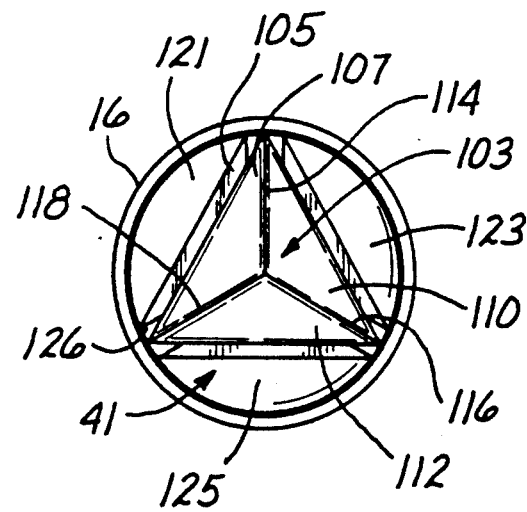
FIG. 7 is an end view of the obturator, shield and cannula associated with another embodiment of the invention.

In this embodiment of the trocar 10, it is of particular advantage that the sharp tip 36 is able to create a puncture, such as the hole 38, which has a diameter sufficiently large to receive not only the shaft 33 of the obturator 32 but also the full diameter of the shield 41. With reference to FIG. 7, it will be noted that the tip 36 has the configuration of a tetrahedron 103 with an apex 105 and lateral surfaces 107, 110 and 112 which face in the distal direction. These surfaces 107, 110 and 112 are flat in a preferred configuration and intersect along lines 114, 116 and 118 which extend proximally and outwardly from the apex 105.

Disposed between the cannula 16 and the shaft 33 is the shield 41. At the distal end of the trocar, this shield 41 transitions from a cylindrical configuration suitable to fit between the cannula 16 and the shaft 33, to a triangular configuration suitable to transition into the tetrahedral configuration associated with the sharp tip 36.

In proximity to the tetrahedron 103, the sheath 41 defines three surfaces 121, 123, and 125 which are associated respectively with the surfaces 107, 110 and 112 of the tip 36. These surfaces 121, 123, and 125 are separated by gaps which are adapted to receive the proximal points of the tetrahedron 103 which extend outwardly to the full radius associated with the shield 41.

The surfaces 121, 123, and 125 are disposed generally in the same plane as the counterpart surfaces 107, 110 and 125 associated with the tetrahedron 103. This provides a continuous ramp for the tissue as the sharp point 36 is inserted through the abdominal wall 12. With the lines 114, 116 and 118 extending out to the full radius of the shield 41, the cut made by the sharp tip 36 is sufficiently large that the shield can enter the hole 38 without significant stretching or tearing of the tissue.

The invention also includes a method for providing the working channel 30 across a body wall, such as the abdominal wall 12. The steps of the process including providing a subassembly including the cannula 16 which forms the working channel 30 and the housing 25 which encloses the seal mechanism 27. The obturator 32 including the elongate shaft 33 having the sharp distal tip 36, is inserted into the working channel 30. The shield 41 having a locked relationship with the obturator 32 protects the seal mechanism during the insertion step. This shield is disposed between the sharp tip 36 and the seal mechanism 27.

Unlocking the shield 41 from the obturator 32 exposes the sharp tip 36 facilitating puncture of the abdominal wall 12 to permit the cannula 13 to extend across this body wall. Finally, the method includes the step of removing the obturator 32 and the shield 41 from the cannula leaving the working channel 30 in operative position across the abdominal wall 12.

The shield 41 can be locked to the subassembly to prevent any significant movement of the shield 41 relative to the subassembly during the puncturing of the abdominal wall. A preferred method may also include the step of unlocking the shield from the subassembly and locking the shield 41 to the obturator 32. These steps in a particular process are timed so that the shield 41 is simultaneously unlocked from the housing 25 and relocked to the obturator 32.

Although the invention has been described with reference to preferred embodiments and methods associated with the concept, it will be apparent that individual elements of structure and steps in the method can be varied all within the scope of the concept. For example, the locking device 61 can be locked to the shaft 31 at any point along this shaft, so long as the length of the tubular section 72 extends from that point to a point distal of the sharp tip 36. Also, the sharp tip 36 can have any solid polygonal configuration as long as it includes a sharp point such as the apex 105. Various interacting parts may also be reversed in a particular embodiment. For example, the inclined surface 90 on the flange 88 of the cap 76 may be provided on the outer surface 64 of the annular flange 63. Interfering parts such as the lug 92 and the shoulder 101 can also be reversed in a particular embodiment.

Due to the wide range of modifications which may be made to the particular disclosed embodiments and methods, one is cautioned to determine the scope of the invention only with reference to the following claims.

We claim:

1. A trocar adapted to provide a working channel through a body wall, comprising:
   a cannula defining the working channel along an axis between the distal and a proximal end of the cannula;
   a housing attached to the cannula at the proximal end of the cannula;
   at least one seal disposed in the housing;
   an elongate obturator adapted to move through the seal in the housing and through the working channel of the cannula, the obturator having a sharp distal tip for puncturing the body wall; and
   a sheath overlying the obturator and movable between a first position wherein the sheath has a releasable fixed relationship with the obturator and extends between the sharp tip and the seal to prevent damage to the seal, and a second position wherein the sheath has a fixed relationship with the housing and the obturator is movable relative to the sheath to expose the sharp tip distally of the cannula.

2. The trocar recited in claim 1 further comprising:
   an annular tongue disposed on one of the sheath and the obturator; and
   an annular groove defined in the other of the sheath and the obturator and adapted to receive the annular tongue for releasibly locking the sheath to the obturator in the first position.

3. The trocar recited in claim 1 further comprising an axial flange having a fixed relationship with the housing and positioned to engage the sheath in the first position and to move the sheath to the second position.

4. The trocar recited in claim 3 wherein the axial flange is an inner annulus and the trocar further comprises:
   an outer annulus carried by the sheath and axially engageable by the inner annulus to release the sheath from the fixed relationship with the obturator.

5. The trocar recited in claim 4 wherein one of the inner annulus and the outer annulus defines a ramp which radially expands the outer annulus to release the sheath from the fixed relationship with the obturator.

6. A trocar adapted to provide a working channel through a body wall, comprising:
   a cannula defining the working channel along an axis between the distal and a proximal end of the cannula;
   a housing attached to the cannula at the proximal end of the cannula;
   at least one seal disposed in the housing;
   an elongate obturator adapted to move through the seal in the housing and through the working channel of the cannula, the obturator having a sharp distal tip for puncturing the body wall;
   a sheath overlying the obturator and movable between a first position wherein the sheath has a fixed relationship with the obturator and a second position wherein the sheath has a fixed relationship with the housing; and
   means responsive to digital movement of the obturator relative to the housing for permitting the sheath to move from the first position to the second position, and responsive to the proximal movement of the obturator relative to the housing for permitting the sheath to move from the second position to the first position.

7. The trocar recited in claim 6 further comprising:
   a tongue disposed on one of the sheath and the obturator; and
   a groove disposed on the other of the sheath and the obturator and configured to receive the tongue to hold the sheath in the first position.

8. The trocar recited in claim 7 wherein the permitting means includes means fixed to the housing for engaging the tongue and removing the tongue in the first position from the groove to permit the sheath to move to the second position and for releasing the tongue in the second position into the groove to permit the sheath to move to the first position.

9. The trocar recited in claim 8 wherein:
   the tongue is disposed on the sheath;
   the groove is defined in the obturator; and
   the engaging means includes an annular flange extending axially of the trocar and having characteristics for radially expanding in response to distal movement of the obturator to remove the tongue from the groove.

10. The trocar recited in claim 8 wherein:
    the tongue is disposed on the sheath;
    the groove is defined in the obturator; and
    the engaging means includes an annular flange extending axially of the trocar and having characteristics for radially contracting the tongue from the second position to engage the groove in the first position.

11. The trocar recited in claim 6 wherein the permitting means is biased to the first position.

12. A method for providing a working channel across a body wall, comprising the steps of:
    providing a subassembly including a trocar housing and a cannula forming the working channel, and a seal mechanism enclosed in the housing;
    inserting into the working channel an obturator having an elongate shaft and a sharp distal tip;
    protecting the seal mechanism during the inserting step with a shield locked to the obturator in a first position wherein the shield is disposed between the sharp tip and the seal mechanism;
    unlocking the shield from the obturator to exposed the sharp tip;
    puncturing the body wall with the sharp tip to permit the cannula to cross the body wall; and
    removing the obturator and the shield from the cannula leaving the working channel in operative position across the body wall.

13. The method recited in claim 12 further comprising the step of locking the shield to the subassembly to prevent any significant movement of the shield relative to the subassembly during the penetrating step.

14. The method recited in claim 13 wherein during the removing step the method further comprises the steps of:
    unlocking the shield from the subassembly; and
    locking the shield to the obturator.

15. The method recited in claim 14 wherein at least a portion of the locking step and the second unlocking step occur generally simultaneously.

16. A trocar adapted to provide a working channel through a body wall, comprising:
    a cannula;
    a housing attached to the cannula and defining with the cannula a working channel;

an elongate obturator having an axis extending between a proximal end and a distal end, the obturator being adapted for movement through the working channel of the housing and cannula;

a sharp tip formed at the distal end of the obturator and having a particular configuration with a plurality of surfaces intersecting along lines which converge to an apex of the sharp distal tip;

a sheath overlying the obturator and having an outer radius and an inner radius, and at least one of the lines of the obturator tip extending proximally to a base point at a radius at least as long as the outer radius of the sheath, the sheath has a distal end defined by a plurality of flat planar surfaces equal in number to the number of surfaces forming the obturator tip; and the flat surfaces being separated by at least one axial opening configured to receive the base point of the obturator tip.

17. The trocar recited in claim 16 wherein the particular configuration includes portions of a tetrahedron.

* * * * *